US011006907B2

(12) United States Patent
Senegas et al.

(10) Patent No.: US 11,006,907 B2
(45) Date of Patent: May 18, 2021

(54) FIELD OF VIEW ADJUSTMENT

(71) Applicant: KONINKLIJKE PHILIPS N.V., Eindhoven (NL)

(72) Inventors: Julien Senegas, Hamburg (DE); Martin Bergtholdt, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/500,865

(22) PCT Filed: Dec. 24, 2018

(86) PCT No.: PCT/EP2018/086841
§ 371 (c)(1),
(2) Date: Oct. 4, 2019

(87) PCT Pub. No.: WO2019/134874
PCT Pub. Date: Jul. 11, 2019

(65) Prior Publication Data
US 2020/0029919 A1    Jan. 30, 2020

(30) Foreign Application Priority Data

Jan. 3, 2018    (EP) .................................... 18150119

(51) Int. Cl.
*A61B 6/00* (2006.01)
*A61B 6/08* (2006.01)
(Continued)

(52) U.S. Cl.
CPC .................. *A61B 6/08* (2013.01); *A61B 6/06* (2013.01); *A61B 6/4417* (2013.01);
(Continued)

(58) Field of Classification Search
CPC ........... A61B 6/06; A61B 6/08; A61B 6/4417; A61B 6/4452; A61B 6/4464; A61B 6/469;
(Continued)

(56) References Cited

U.S. PATENT DOCUMENTS

2002/0054662 A1    5/2002  Verdonck
2014/0169652 A1    6/2014  Vic
(Continued)

FOREIGN PATENT DOCUMENTS

DE    102012201798 A1    8/2013
WO    WO2016156150 A1    10/2016
WO    WO2017076841 A1    5/2017

OTHER PUBLICATIONS

PCT International Search Report, International application No. PCT/EP2018/086841, dated Mar. 15, 2019.

*Primary Examiner* — Dani Fox
(74) *Attorney, Agent, or Firm* — Larry Liberchuk

(57) ABSTRACT

The appropriate positioning of a patient in an X-Ray imaging system can present difficulties for medical professional owing, on one hand to the small size of important anatomical aspects which need to be captured in X-Ray images, and on the other hand to the significant movements in a field of view presented by a typical patient. The present application proposes to obtain an image of the position of a patient in the field of view at approximately the same time that an initial X-Ray image is obtained. If it proves necessary to obtain a subsequent X-Ray image with updated field of view settings (for example, collimation parameters), the movement of the patient at the point of taking the second image is factored into the provision of updated field of view settings.

14 Claims, 3 Drawing Sheets

(51) Int. Cl.
*A61B 6/06* (2006.01)
*A61B 5/00* (2006.01)

(52) U.S. Cl.
CPC .......... *A61B 6/4452* (2013.01); *A61B 6/4464* (2013.01); *A61B 6/469* (2013.01); *A61B 6/527* (2013.01); *A61B 6/545* (2013.01); *A61B 6/582* (2013.01); *A61B 5/0077* (2013.01)

(58) Field of Classification Search
CPC ....... A61B 6/488; A61B 6/5211; A61B 6/527; A61B 6/5294; A61B 6/545; A61B 6/547; A61B 6/582; A61B 6/586; A61B 5/0077; G16H 50/20
See application file for complete search history.

(56) References Cited

U.S. PATENT DOCUMENTS

| | | |
|---|---|---|
| 2015/0085971 A1 | 3/2015 | Braun |
| 2015/0228071 A1 | 8/2015 | Jockel |
| 2015/0327821 A1 | 11/2015 | Hu |
| 2015/0327830 A1 | 11/2015 | Hu |
| 2016/0262715 A1 | 9/2016 | Charnegie |
| 2017/0055925 A1 | 3/2017 | Lee |
| 2017/0065238 A1 | 3/2017 | Smith |
| 2017/0100089 A1 | 4/2017 | Chang |

FIELD OF VIEW ADJUSTMENT

FIELD OF THE INVENTION

This invention relates generally to an apparatus for adjusting the field of view of an X-Ray imaging system, an X-Ray imaging system, a method for adjusting a field of view of an X-Ray imaging system, a computer program element, and computer readable medium.

BACKGROUND OF THE INVENTION

A frequent occurrence in the field of radiology is a need to re-take an X-Ray image, when a preliminary X-Ray image has been obtained with important anatomical features missing. This case typically occurs as a result of an X-Ray apparatus being set to provide undesirable field of view settings (for example, an incorrectly set collimator), in relation to the physical position of a patient, where defects with these settings were not identified prior to the acquisition of the preliminary X-Ray image. Patient motion out of the field of view also leads to field of view setting errors.

US 2015/0228071 A1 discusses an X-Ray imaging approach which uses a spatial depth information to update an image collimation window. Such approaches may, however, be further improved.

SUMMARY OF THE INVENTION

There may, therefore, be a need to provide an apparatus which reduces the burden on X-Ray radiology department personnel, and their patients, during X-Ray acquisition protocols.

The object of the present invention is solved by the subject-matter of the independent claims. Further embodiments are incorporated in the dependent claims.

According to a first aspect, there is provided an apparatus for adjusting the field of view of an X-ray imaging system comprising:
   an input unit; and
   a processing unit.

The input unit is configured to acquire (i) initial patient position image data of a patient in an initial position from a patient position camera based in a first coordinate system of a patient position camera and (ii) to acquire initial X-ray image data of the patient from an X-ray system configured into an initial field of view setting, wherein the initial patient position image data and the initial X-ray image data are acquired substantially simultaneously.

The processing unit is configured to detect a portion of an item of patient anatomy in the initial X-ray image data, to predict an improved field of view setting for enhanced imaging of the item of patient anatomy in a second coordinate system of the initial X-ray image data, wherein the prediction is provided using an anatomical model, to obtain subsequent patient position image data from the patient position camera, to generate patient position error data by comparing the subsequent patient position image data with the initial patient position image data, and to provide a subsequent field of view setting based on the patient position error data and the improved field of view setting.

Accordingly, it is proposed to combine patient position image data and initial X-Ray image data acquired at the substantially the same time, and by correcting for the difference in the respective coordinate systems of the camera used to acquire patient position image data and the X-Ray system, to provide field of view settings to an X-Ray system that improve a subsequent X-Ray patient image.

Optionally, the processing unit is further configured to transform the improved field of view setting from the second coordinate system into the first coordinate system, wherein the subsequent field of view setting is based on the transformed improved field of view setting.

Optionally, the processing unit is further configured to provide the subsequent field of view setting by transforming the patient position error data from the first coordinate system into the second coordinate system, and combining the improved field of view setting with the transformed patient position error data to form the subsequent field of view setting.

Accordingly, the camera used to acquire patient position error data may be in a first coordinate system different to that of the X-Ray source and detector pair located in a second coordinate system.

Optionally, the processing unit is further configured to provide the improved field of view setting as a bounding box in the second coordinate system bounding an element in the anatomical model.

Accordingly, a proposed correction to the field of view setting of an X-Ray imaging system may be computed in the spatial domain of the X-Ray image.

Optionally, the apparatus further comprises an output unit. The output unit is further configured to output an X-ray system configuration command based on the subsequent field of view setting.

Accordingly, the field of view of an X-Ray system may be adjusted dependent on the calculations performed by the apparatus.

Optionally, the X-ray system configuration command comprises one, or a plurality, of X-ray source collimator parameter data, X-ray source tilt data, X-ray source pan data, X-ray source X-translation data, X-ray source Y-translation data, X-ray source Z-translation data, X-ray detector X-translation data, X-ray detector Y-translation data, X-ray detector Z-translation.

Optionally, the processing unit is further configured to calibrate the first coordinate system of the patient position camera in relation to the second coordinate system of the initial X-ray image data.

Accordingly, an improvement in accuracy between the patient position error data is observed.

Optionally, the processing unit is further configured to acquire patient position image data continuously, and to calculate continuously the patient position error data, and the subsequent field of view setting.

Accordingly, the subsequent field of view setting may be provided with a minimal latency.

Optionally, the input unit is further configured to receive X-ray examination protocol data. The processing unit is further configured to generate the initial field of view setting based on the X-ray examination protocol, and to generate the prediction of the improved field of view setting based additionally on the X-ray examination protocol data.

According to a second aspect, there is provided an X-ray imaging system comprising:
   an X-ray source configured to expose a region of interest of a patient to X-ray radiation;
   an X-ray detector configured to receive X-ray radiation emitted by the X-ray source to thus provide X-ray image data of a patient; and
   a patient imaging camera configured to obtain patient position image data of the region of interest of a patient; and
   an apparatus according to the first aspect.

The input unit of the apparatus is configured to acquire initial patient position image data of a patient in an initial position from the patient position camera, and to acquire initial X-ray image data of the patient from the X-ray detector.

The X-ray source and/or the X-ray detector are configurable into an initial and subsequent view state based upon an initial and a subsequent field of view setting generated by the apparatus.

Optionally, the patient imaging camera is a video camera, an infra-red camera, or a depth camera.

Accordingly, 3D data acquired from depth camera, and anatomical data extracted from the first X-Ray image using the anatomical model may be combined to obtain a subsequent field of view setting having an improved accuracy.

Optionally, the system according to the second aspect further comprises a multi-view camera system comprising a plurality of cameras wherein the initial patient position image data is provided using the multi-view camera system.

A multi-view camera system provides better spatial resolution of a patient in a field of interest, thus improving the accuracy of a subsequent field of view setting.

Optionally, the subsequent field of view setting is set to provide a field of view that is entirely outside (exclusive of) of the initial field of view.

Optionally, the subsequent field of view setting is set to provide a field of view that overlaps with the initial field of view.

According to a third aspect, there is provided a method for adjusting a field of view of an X-ray imaging system comprising:
a) acquiring initial patient position image data of a patient in an initial position from a patient position camera based in a first coordinate system of the patient position camera,
b) acquiring initial X-ray image data of the patient from an X-ray system configured into an initial field of view setting, wherein the initial patient position image data and the initial X-ray image data are acquired substantially simultaneously;
c) detecting a portion of an item of patient anatomy in the initial X-ray image data;
d) predicting an improved field of view setting for enhanced imaging of the item of patient anatomy in a second coordinate system of the initial X-ray image data, wherein the prediction is provided using an anatomical model;
e) obtaining subsequent patient position image data from the patient position camera;
f) generating patient position error data by comparing the subsequent patient position image data with the initial patient position image data; and
g) providing a subsequent field of view setting based on the patient position error data and the improved field of view setting.

Optionally, providing a subsequent field of view setting further comprises:
g2) transforming the patient position error data from the first coordinate system into the second coordinate system;
g3) combining the improved field of view setting with the transformed patient position error data to form the subsequent field of view setting.

According to a fourth aspect, there is provided a computer program element for controlling a processing unit and/or system as according to the first and/or second aspects, which, when the computer program element is executed by the processing unit and/or system, is adapted to perform the method of the third aspect.

According to a fifth aspect, computer readable medium having stored the computer program element of the fourth aspect.

In the following application, the term "field of view of an X-Ray imaging system" refers to a portion of the region of interest of a patient that an X-Ray image captures during a typical exposure. The field of view of an X-Ray imaging system is generically defined by the distance of an X-Ray source from an X-Ray detector, and the characteristics of the X-Ray detector and the X-Ray source aperture. In a simple case, the field of view may be adjusted by placing a collimator (which may have one or a plurality of shutters) in the beam-path between the X-Ray source and the X-Ray detector. Another way of adjusting the field of view is by tilting (adjusting the vertical angle with respect to the X-Ray detector) and/or panning (adjusting the horizontal angle with respect to the X-Ray detector) the X-Ray source. Another way of adjusting the field of view is by horizontally and/or vertically translating either or both of the X-Ray source and/or the X-Ray detector in relation to each other. Another way of adjusting the field of view is by increasing or decreasing the distance separation between the X-Ray source and X-Ray detector.

It will be appreciated that the variation of all, or a subset, of the parameters discussed in the previous paragraph, may cause anatomical features detected by the X-Ray detector to move out of, or into, the field of view. Accordingly, the data required to set an X-Ray system with an appropriate field of view is referred to as "field of view data".

The term "field of view data" may, for example, comprise stepper motor position instructions to set one or more of a collimator member, or positioning motors defining the pan, tilt, distance separation, vertical and horizontal position of the X-Ray detector and/or X-Ray source.

In the following application, the term "initial patient position image data" refers to, for example, an image or video of a patient standing in a target region of an X-Ray system at the instant at which an initial X-Ray image is acquired. The initial patient position image data is acquired via a patient position camera located in a first coordinate system that is different to a coordinate system of the X-Ray source and X-Ray detector pair of the X-Ray imaging system. The initial patient position image data is acquired, for example, within 1 ms, 10 ms, or 100 ms of an initial X-Ray image being taken, and for the purposes of this application, the term "substantially simultaneously" is within these time ranges.

In the following application, the term "anatomical model" refers to a data structure, typically stored and executed on processing unit (such as a computer). The anatomical model typically contains information defining a location and shape of common anatomical features of patients. For example, a typical anatomical model contains a representation of structures such as lungs, rib bones, spine, for example, and the likelihood that a certain anatomical element is present in a certain position. The anatomical model is typically designed to allow anatomical elements to be identified from incomplete portions of an image of an organ.

In the following application, the term "patient position error data" refers to the tracking of a subsequent patient position starting from an initial patient position using a patient position camera located in a first coordinate system. For example, if a patient takes a step towards an X-Ray imaging detector after the initial X-Ray image has been obtained, the patient position error data likewise reflects that the patient is now one step closer to the X-Ray detector and one step further away from the X-Ray source (once the transformation from the first coordinate system to the second corner system has been made).

Accordingly, it is a basic idea of the application to capture an initial patient position at a time when a first X-Ray image is obtained. Tracking of patient movement using a patient camera enables the calculation of a real-time update of the field of view necessary for an anatomical portion of interest to be correctly imaged, to thus enable a second X-Ray exposure to be more successful. In other words, it is proposed to obtain an image of the position of a patient in the field of view at approximately the same time that an initial X-Ray image is obtained. If it proves necessary to obtain a subsequent X-Ray image with updated field of view settings (for example, collimation parameters), the movement of the patient at the point of taking the second image is factored into the provision of updated field of view settings.

BRIEF DESCRIPTION OF THE DRAWINGS

Exemplary embodiments of the invention will now be described with reference to the following drawings.

DETAILED DESCRIPTION OF EMBODIMENTS

In radiography examinations, a requirement is to position the patient accurately with respect to the X-Ray detector and X-Ray source, and then to adapt the system's geometry configuration and X-Ray system parameters to the patient's anatomy. As an example, the size and shape of collimation window in an X-Ray source should be adapted to fit the size of a body part to be imaged.

Even assuming that the technical operator is well experienced, frequently the target anatomy is not completely included in the final X-Ray image. Important anatomical structures are, therefore, missing. Typical causes may include an incorrect collimation window setting, the positioning of the patient in relation to the X-Ray source and/or X-Ray detector, or the voluntary or involuntary movement of a patient shortly before image acquisition. Other field of view errors can arise from patient motion.

If an X-Ray image is obtained which excludes too much of an anatomical area having diagnostic importance, a subsequent X-Ray image needs to be taken. Currently, little or no feedback is given to an X-Ray system operator to find improved field of view (such as collimation) settings. Often, in difficult cases, several retakes are necessary to obtain a satisfactory image. This increases the radiation exposure that the patient is subjected to, and maybe an uncomfortable experience for the patients, implying longer examination times and delays in hospital procedures.

Figure 1:
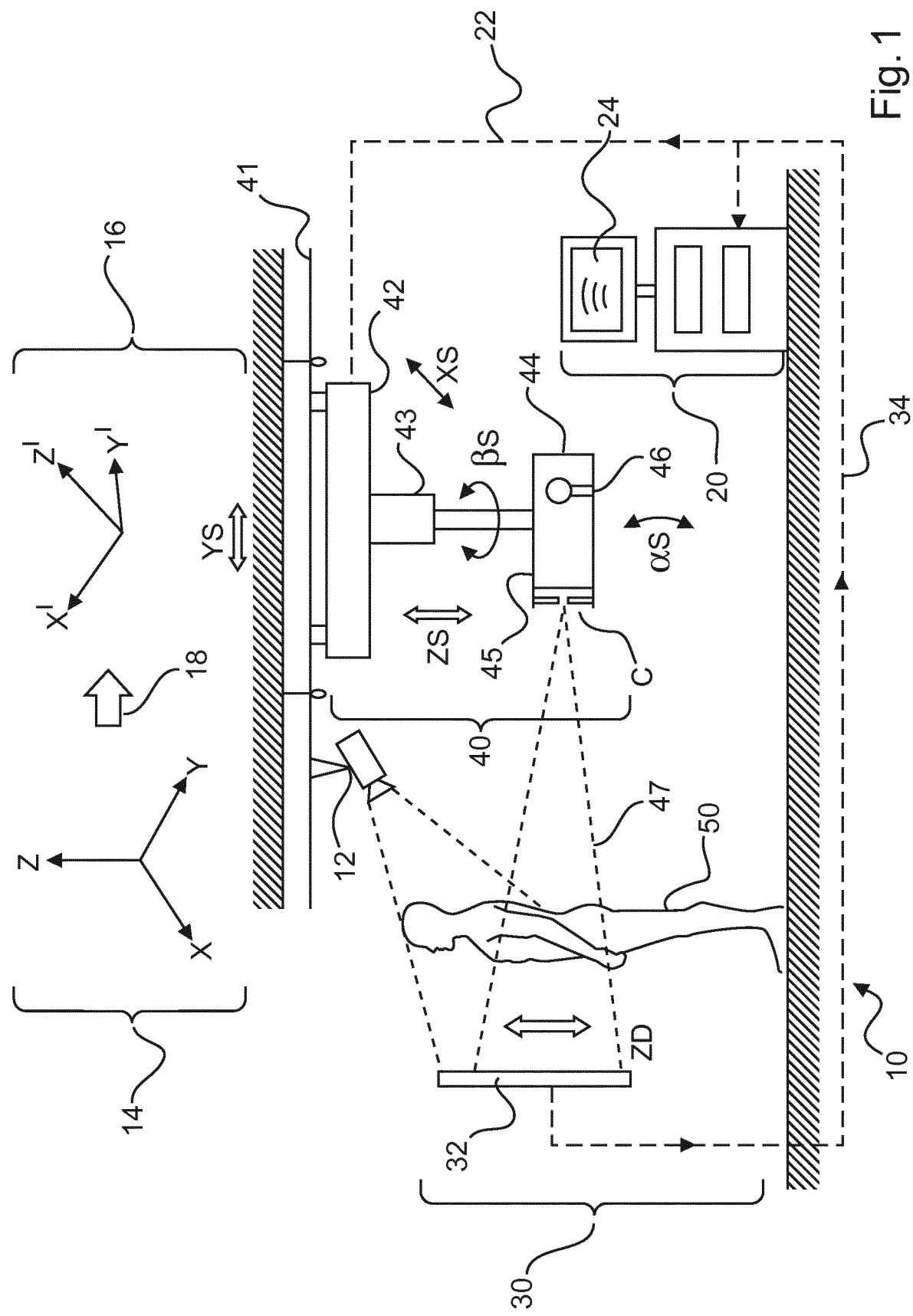
FIG. 1 illustrates a schematic side elevation of an X-Ray imaging system.

FIG. 1 illustrates a schematic side elevation of an exemplary X-Ray imaging system 10 in accordance with the second aspect, to provide context for the following discussion. It will, however, be appreciated that many X-Ray imaging systems may be provided falling within the scope of the present claims.

In FIG. 1, a patient is shown in the process of having an X-Ray image taken in one of the most common projection geometries in clinical radiography, the posterior-anterior view of the chest.

The X-Ray imaging system 10 comprises a control apparatus 20, a X-Ray detector 30 and an X-Ray source 40. A patient 50 typically stands in the region of interest in-between the X-Ray source 40 and the X-Ray detector 30.

The X-Ray imaging source 40 is supported on a dolly 42 configured to slide along roof rails 41 in an X-Ray imaging suite. This enables translational movement of the X-Ray source 40 towards, or away from, the patient 50 (dimension YS). The X-Ray imaging source 40 is suspended from the dolly 42 by a support member 43. The support member 43 is movable in an up or down direction (towards and away from the floor, direction ZS). Optionally, the X-Ray imaging source 40 is also azimuthally rotatable around the axis of support member 43 ($\beta$S), and tiltable ($\alpha$S).

An X-Ray imaging source assembly 44 is attached to support member 43 and comprises a substantially X-Ray radiation sealed enclosure 45, with an X-Ray emitter 46 inside (typically, the X-Ray emitter 46 is a rotating anode X-Ray emitter). However, the enclosure 45 is configured to allow the emission of an X-Ray beam towards a patient 50. The X-Ray enclosure 45 also comprises a collimation window C, with motor-driven shutters enabling control of the shape of the emitted X-Ray beam. The X-Ray imaging source 40 is controlled using data signals from the control apparatus 20, transmitted via digital datalink 22.

The X-Ray detector 30 may comprise, for example, a digital flat panel detector 32 arranged to receive an X-Ray beam 47 emitted from the X-Ray source 40. The X-Ray detector 30 transmits X-Ray image data to control apparatus 20 using the digital data link 34. Although not shown in FIG. 1, X-Ray detector 30 may optionally also be arranged on a servomotor actuated arrangement to enable tilting, and horizontal and vertical translation.

The relative positioning of the X-Ray source 40 and the X-Ray detector 30 in the X-Ray imaging suite and, for example, collimation settings, results in an overall field of view of the X-Ray system. In a hypothetical case that the collimator C is set to limit the field of view on the left-hand side of the patient in the posterior anterior view, and the patient takes a side-step to their left, then the patient would reposition themselves enough within the field of view to prevent correct imaging of an anatomical item of interest.

As an extreme example, positioning the X-Ray source enclosure 45 close to the ceiling, with a substantial downward tilt $\alpha$S, results in the field of view having a significant "keystone" effect.

The X-Ray imaging system 10 illustrated in FIG. 1 also comprises a patient imaging camera 12. The patient imaging camera 12 is preferably a depth camera, but may also be a standard video camera or infrared camera. The patient imaging camera 12 is shown here as imaging the patient from the roof rail 41, although it will be appreciated that the patient imaging camera 12 may be placed substantially anywhere in the X-Ray imaging suite having an unobstructed view of the patient 50. Notably, the patient imaging camera 12 is in a first coordinate system 14, that is different from a second coordinate system 16 defined by the X-Ray source 40 and detector 30. For example, as a result of differing alignment between the patient imaging camera 12 and the X-Ray imaging system 10, the first coordinate system is offset at an angle from the second coordinate system. Thus, a transformation between the first and second coordinate systems would be a counter-offset of the same magnitude. More complex coordinate transformations could be provided, for example, a diverging coordinate system (to account for a divergence or "keystone" effect caused by a ceiling-mounting of the patient imaging camera).

It will be appreciated that for the purposes of accuracy at an anatomical scale, placement of the patient imaging camera 12 directly upon the X-Ray source enclosure 45 and/or directly upon the X-Ray detector 30 may still be considered to result in a coordinate system that is "significantly different".

Therefore, for any placement of the patient imaging camera 12, there exists a coordinate transformation 18 between the frame of reference of the patient imaging camera 12 and the frame of reference of the X-Ray source 40 and X-Ray detector 30.

Turning now to an apparatus 20 for adjusting the field of view of an X-Ray imaging system, there is provided according to the first aspect an apparatus for adjusting the field of view of an X-ray imaging system. The apparatus 20 comprises:

an input unit 22; and
a processing unit 24.

The input unit 22 is configured to acquire (i) initial patient position image data of a patient in an initial position from a patient position camera based in a first coordinate system of a patient position camera and (ii) to acquire initial X-ray image data of the patient from an X-ray system configured into an initial field of view setting, wherein the initial patient position image data and the initial X-ray image data are acquired substantially simultaneously.

The processing unit 24 is configured to detect a portion of an item of patient anatomy in the initial X-ray image data, to predict an improved field of view setting for enhanced imaging of the item of patient anatomy in a second coordinate system of the initial X-ray image data, wherein the prediction is provided using an anatomical model, to obtain subsequent patient position image data from the patient position camera, to generate patient position error data by comparing the subsequent patient position image data with the initial patient position image data, and to provide a subsequent field of view setting based on the patient position error data and the improved field of view setting.

Figure 2:
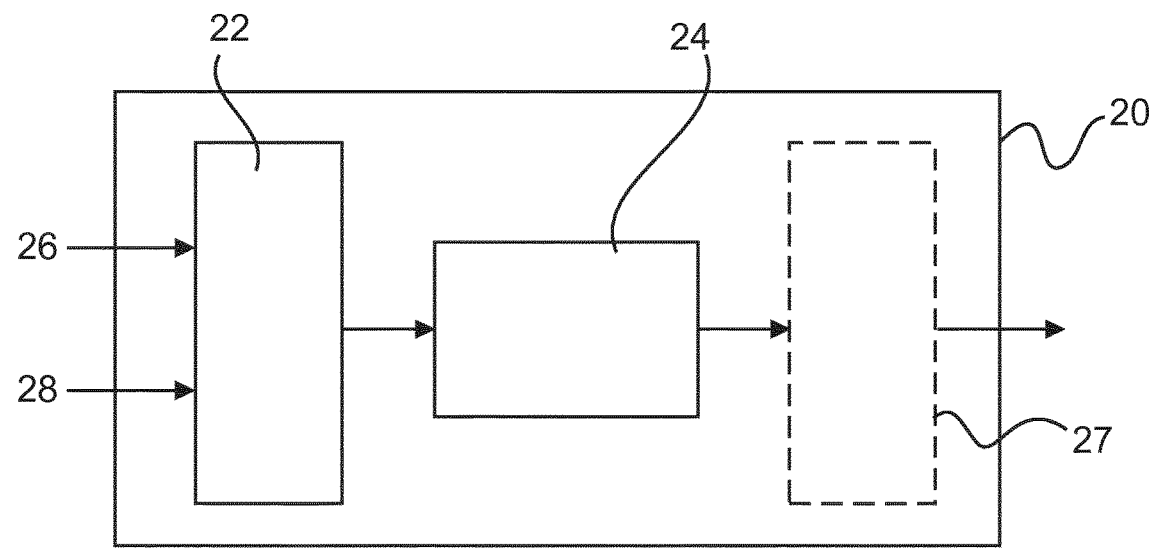
FIG. 2 schematically illustrates an apparatus in accordance with the first aspect.
Figure 4:
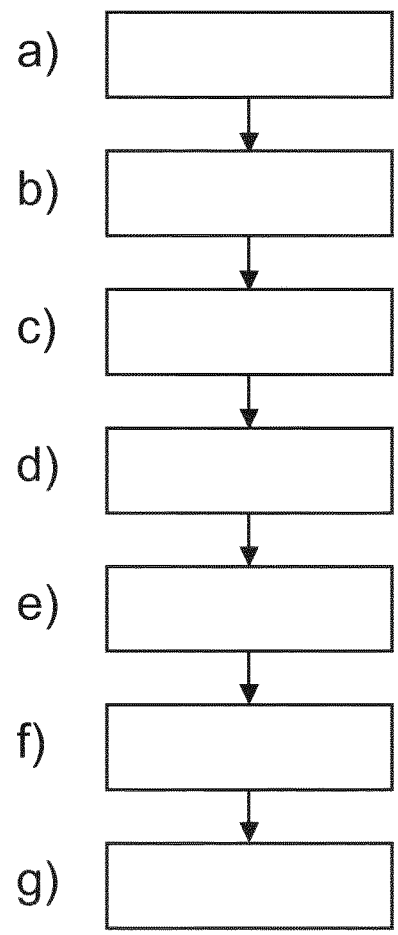
FIG. 4 schematically illustrates a method in accordance with the third aspect.

FIG. 2 schematically illustrates an apparatus according to the first aspect.

The apparatus 20 illustrated in FIG. 2 comprises an input unit 22 and a processing unit 24. The apparatus 20 functions as a data processor, and may be implemented, for example, as software executing upon a general-purpose computer, an embedded microprocessor, a digital signal processor, a field programmable gate array, a combination of these, or alternatives known to the person skilled in the art.

A specific example now to be discussed concerns an embodiment in which the field of view of the X-Ray system is defined by collimation settings only, although the calculation of the field of view setting, can, of course, be extended dependent on the particular type and geometry of X-Ray system used.

Initial X-Ray image data 26 acquired from an X-Ray detector, such as a flat panel digital detector is acquired by the input unit 22 at substantially the same time instant as initial patient position image data 28. The X-Ray system is configured into an initial view setting at this time. In practice, a variation in the acquisition time of the initial X-Ray image data 26 and the patient position image data 28 around 1 ms, 10 ms, or 100 ms is permissible without significant deterioration in performance.

Optionally, the processing unit 24 may perform various pre-processing operations to format the initial X-Ray image data 26 and/or the initial patient position image data 28, such as contrast correction and/or denoising the images.

The processing unit 24 executes an image analysis subroutine that enables a portion of an item of patient anatomy in the initial X-Ray image data 26 to be identified. For example, an edge detection algorithm may be applied to the initial X-Ray image data 26, and then a comparison with an anatomical model may be made. Points in the initial X-Ray image data 26 suffering from a collimation error will be identified as a point having a sharp, unanatomical edge compared to a similar point in the anatomical model, enabling detection of a portion of an item patient anatomy in the initial X-Ray image data 26.

The detection of the portion of an item of patient anatomy is related to the initial X-Ray image data 26 which is in a second coordinate system (the coordinate system of the X-Ray acquisition system).

Subsequently, a prediction of an improved field of view setting is obtained. For example, a comparison of the anatomical model with the detected portion of item of patient anatomy in the initial X-Ray image data may be made. A bounding box in the second coordinate space of the X-Ray image data 26 may be generated using the anatomical model to indicate how the field of view should be updated to enable an anatomical feature (such as a truncated lung) to be identified in its entirety. A set of updated coordinates in the second coordinate space are thus obtained, forming a prediction of an improved field of view setting.

Between the time that the initial X-Ray image data 26 was obtained, and the taking of a subsequent X-Ray image with updated field of view settings, it is likely that the patient will have moved. Thus, simply computing a new field of view setting by transforming the bounding box coordinates into (in this case) collimation settings would not be enough to yield a good quality final image, because such collimation settings would not take into account the additional error caused by the movement of the patient after the initial X-Ray image data 26 had been obtained.

Accordingly, at a time as close as possible to the acquisition of subsequent X-Ray image data using the improved field of view setting, subsequent patient position image data is obtained from the patient position camera. The purpose of the subsequent patient position image is to identify the relative motion of the patient starting from the patient position at the time of obtaining the initial patient position image data, and ending with a time as close as possible to the acquisition of subsequent X-Ray image data using the improved field of view setting.

It will be appreciated by the skilled person that wide variety of image and/or video processing techniques may be used to generate the patient position data, for example a technique such as optical flow, feature point tracking, landmark detection and tracking, fitting of 3D surface models (optionally derived from a previous patient imaging scan).

Notably, the patient position error data is captured in the first coordinate system of the patient position camera. As noted previously, the prediction of the improved field of view setting is, in this example, present in the second coordinate system of the X-Ray imaging system.

Preferably, the prediction of the improved field of view setting (for example, the coordinates of the bounding box) are transformed into the first coordinate system of the patient position camera and compared. In particular, if further movement of the patient results in a lack of correspondence between the bounding box and the patient, a subsequent field of view setting based on the patient position error data and the improved field of view setting is generated.

A simple example of a suitable transform is a rotation matrix, although many other coordinate transformation techniques may be applied, such as a divergence between the first and second coordinate systems (useful for addressing "keystone" effects arising from positioning of the patient imaging camera 12 at a steep inclined angle in relation to a patient).

In another example, the patient position error data in its first coordinate system may be transformed into the second coordinate system of the X-Ray imaging system.

In another example, both the patient position error data in its first coordinate system and the improved field of view setting in its second coordinate system may be transformed into a third coordinate system. Notably, the patient position camera position and the X-Ray system position is calibrated before use so that the coordinate transformation necessary to convert between the first coordinate system and the second coordinate system can be obtained.

Optionally, the apparatus 20 communicates the improved field of view setting to an X-Ray imaging system in preparation for the acquisition of subsequent X-Ray imaging data.

Optionally, the apparatus 20 instructs the X-Ray imaging system to obtain subsequent X-Ray imaging data based on the improved field of view setting.

Optionally, the apparatus 20 provides visual feedback to the operator (for example, via a display signal to a screen of an X-Ray system) to instruct the operator either to manually change the field of view of the system (for example, by changing the collimation parameters) and/or in extreme cases to move the patient.

Optionally, the patient position camera tracks additional patient motion, which is used to compute an updated position of the patient. The collimation parameters may be updated in real-time according to the transformation between the first coordinate system and the second coordinate system.

Accordingly, an image acquisition approach has been described which uses a feedback loop between an initial patient position image data 28 and anatomical data extracted from initial X-Ray image data 26.

In another example of this approach, the patient position camera is a depth camera, such as a structured light camera capable of combining depth data and video data.

In this example, a depth camera, providing depth data and regular video data at a suitable frame rate is positioned so as to image the examination area with minimal obstruction.

Then, when the camera position and orientation have been calibrated with respect to the geometry of the radiography system, points in the camera geometry can be mapped into the X-Ray system geometry and vice-versa.

Subsequently, a depth image of the patient and a patient position image (video) is acquired substantially simultaneously with the initial X-Ray image data.

The position and shape of the target anatomy is automatically detected in the X-Ray image. If anatomical structures are missing in the obtained X-Ray image (obtained at a first collimation setting) their most likely position is predicted based on prior anatomical knowledge, for example from a statistical anatomical model. A bounding box showing the optimal location of missing anatomical structures is obtained using the anatomical model in comparison with the initial X-Ray image data.

Using the coordinate transformation between the first coordinate system and the second coordinate system computed in the calibration step, the coordinates of the bounding box are transformed into the patient position camera's coordinate system, and compared with the acquired depth data.

Then, an optimal field of view parameter (in this case, a collimation setting) is derived from the correspondence between the bounding box and the acquired depth data. The X-Ray system collimator is updated with these settings.

Figure 3:
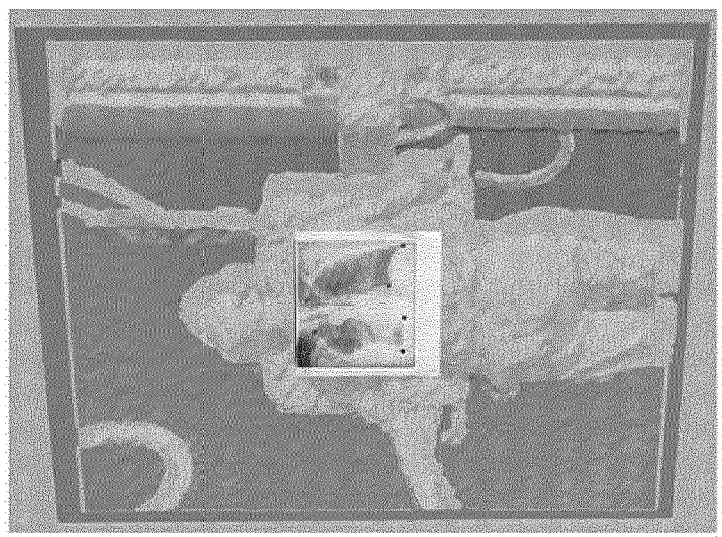
FIG. 3 shows examples of patient positioning.
Figure 3:
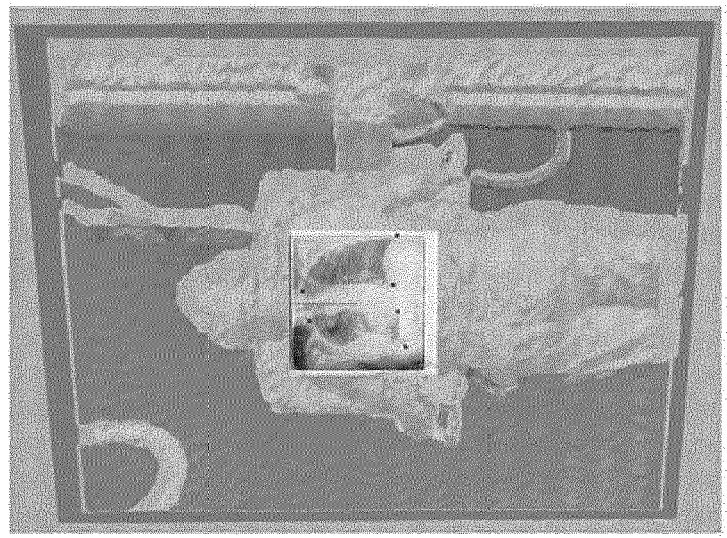
Figure 3:
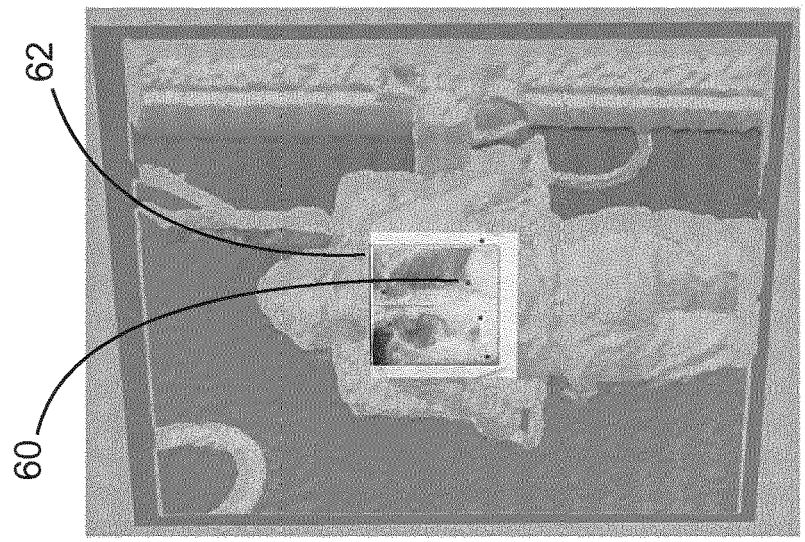

FIG. 3 illustrates a problem solved by the present invention.

FIG. 3a) shows the acquisition of initial X-Ray image data. In this case, the right lung 60 was cropped because the collimation window 62 was too narrow and the patient was not centrally positioned.

FIGS. 3b) and 3c) illustrates first and second retakes needed to obtain the final FIG. 3c), including re-setting the collimation parameters and re-positioning the patient.

According to the present aspects, a correspondence between internal anatomical structures and patient image data (for example, 2D image data and/or 3D surface data) can be used immediately after the first acquisition the compute the optimal position and examination parameters for the retake.

It will be appreciated that aspects of the present invention have wide applicability to X-Ray systems involving a variable field of view where the movement of a patient is a risk to image quality. The technique is also applicable to fluoroscopy X-Ray imaging, for example. According to a second aspect, there is provided an X-ray imaging system comprising:

an X-ray source 40 configured to expose a region of interest of a patient to X-ray radiation;

an X-ray detector 30 configured to receive X-ray radiation emitted by the X-ray source 40 to thus provide X-ray image data of a patient; and a patient imaging camera 12 configured to obtain patient position image data of the region of interest of a patient; and an apparatus 20 according to the first aspect.

The input unit of the apparatus is configured to acquire initial patient position image data of a patient in an initial position from the patient position camera, and to acquire initial X-ray image data of the patient from the X-ray detector.

The X-ray source 40 and/or the X-ray detector 30 are configurable into an initial and subsequent view state based upon an initial and a subsequent field of view setting generated by the apparatus 20.

Optionally, the patient imaging camera is a video camera, an infra-red camera, or a depth camera.

Accordingly, a comparison may be made between 3D data acquired from depth camera, and anatomical data extracted from the first X-Ray image using the anatomical model. This improves the accuracy of the subsequent field of view setting.

Optionally, the system according to the second aspect further comprises a multi-view camera system comprising a plurality of cameras wherein the initial patient position image data is provided using the multi-view camera system.

A multi-view camera system provides better spatial resolution of a patient in a field of interest, thus improving the accuracy of a subsequent field of view setting.

Optionally, in the third aspect providing a subsequent field of view setting further comprises:

g1) transforming the improved field of view setting from the second coordinate system into the first coordinate system, wherein the subsequent field of view setting is based on the transformed improved field of view setting.

Optionally, in the third aspect providing the improved field of view setting provided as a bounding box in the second coordinate system bounding an element in the anatomical model.

Optionally, the third aspect comprises outputting X-ray system configuration commands based on the subsequent field of view setting.

Optionally, in the third aspect the X-ray system configuration commands comprise one, or a combination, of:

h1) X-ray source collimator parameters;
h2) X-ray source tilt data;
h3) X-ray source pan data;
h4) X-ray source X-translation data;
h5) X-ray source Y-translation data;
h6) X-ray source Z-translation data;
h7) X-ray detector X-translation data;
h8) X-ray detector Y-translation data; and
h9) X-ray detector Z-translation data.

Optionally, in the third aspect the patient position camera is a video camera, an infra-red camera, or a depth camera.

Optionally, in the third aspect the initial patient position image data is provided using a multi-view camera system comprising a plurality of cameras.

Optionally, the third aspect further comprises:
b1) calibrating the first coordinate system of the patient position camera in relation to the second coordinate system of the initial X-ray image data.

Optionally, in the third aspect patient position image data is acquired continuously, to enable the patient position error data, and the subsequent field of view setting, to be calculated continuously.

Optionally, the third aspect further comprises:
a1) loading an X-ray examination protocol;
wherein in step a), the initial field of view setting is generated based on the X-ray examination protocol; and
wherein in step d), the prediction of the improved field of view setting is generated based additionally on the X-ray examination protocol.

A computer program element in accordance with the fourth aspect might be stored on a computer unit, which might also be an embodiment of the present invention. This computing unit may be adapted to perform or induce performance of the steps of the method described above. Moreover, it may be adapted to operate the components of the above-described apparatus.

The computing unit can be adapted to operate automatically and/or execute orders of a user. A computer program may be loaded into the working memory of a data processor. The data processor may thus be equipped to carry out the method of the invention.

This exemplary embodiment of the invention covers both the computer program that has the invention installed from the beginning, and a computer program that by means of an update turns an existing program into a program that uses the invention. A computer program may be stored and/or distributed on a suitable medium, such as an optical storage medium, or a solid state medium supplied together with, or as part of other hardware, but may also be distributed in other forms, such as via the Internet or other wired or wireless telecommunication systems.

However, the computer program may also be presented over a network like the World Wide Web, and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type claims, whereas other embodiments are described with reference to device-type claims. However, a person skilled in the art will gather from the above, and the following description that, unless otherwise notified, in addition to any combination of features belonging to one type of subject-matter, other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An apparatus for adjusting the field of view of an X-ray imaging system, comprising:
    an input unit; and
    a processing unit;
    wherein the input unit is configured to acquire initial patient position image data of a patient in an initial position from a patient position camera based in a first coordinate system of a patient position camera and to acquire initial X-ray image data of the patient from an X-ray system configured into an initial field of view setting,
    wherein the initial patient position image data and the initial X-ray image data are acquired substantially simultaneously;
    wherein the processing unit is configured to detect a portion of an item of patient anatomy in the initial X-ray image data, to predict an improved field of view setting for enhanced imaging of the item of patient anatomy in a second coordinate system of the initial X-ray image data, wherein the prediction is provided using an anatomical model, to obtain subsequent patient position image data from the patient position camera, to generate patient position error data by comparing the subsequent patient position image data with the initial patient position image data, and to provide a subsequent field of view setting based on the patient position error data and the improved field of view setting.

2. The apparatus according to claim 1,
    wherein the processing unit is further configured to transform the improved field of view setting from the second coordinate system into the first coordinate system, wherein the subsequent field of view setting is based on the transformed improved field of view setting.

3. The apparatus according to claim 1,
    wherein the processing unit is further configured to provide the subsequent field of view setting by transforming the patient position error data from the first coordinate system into the second coordinate system, and combining the improved field of view setting with the transformed patient position error data to form the subsequent field of view setting.

4. The apparatus according to claim 2,
wherein the processing unit is further configured to provide the improved field of view setting as a bounding box in the second coordinate system bounding an element in the anatomical model.

5. The apparatus according to claim 1, further comprising:
an output unit;
wherein the output unit is further configured to output an X-ray system configuration command based on the subsequent field of view setting.

6. The apparatus according to claim 5,
wherein the X-ray system configuration command comprises one of X-ray source collimator parameter data, X-ray source tilt data, X-ray source pan data, X-ray source X-translation data, X-ray source Y-translation data, X-ray source Z-translation data, X-ray detector X-translation data, X-ray detector Y-translation data, X-ray detector Z-translation.

7. The apparatus according to claim 1,
wherein the processing unit is further configured to calibrate the first coordinate system of the patient position camera in relation to the second coordinate system of the initial X-ray image data.

8. The apparatus according to claim 1,
wherein the processing unit is further configured to acquire patient position image data continuously, and to calculate continuously the patient position error data, and the subsequent field of view setting.

9. The apparatus according to claim 1,
wherein the input unit is further configured to receive X-ray examination protocol data; and
wherein the processing unit is further configured to generate the initial field of view setting based on the X-ray examination protocol, and to generate the prediction of the improved field of view setting based additionally on the X-ray examination protocol data.

10. An X-ray imaging system comprising:
an X-ray source configured to expose a region of interest of a patient to X-ray radiation;
an X-ray detector configured to receive X-ray radiation emitted by the X-ray source to thus provide X-ray image data of a patient;
a patient imaging camera configured to obtain patient position image data of the region of interest of a patient; and
an apparatus for adjusting the field of view of an X-ray imaging system, comprising:
an input unit; and
a processing unit;
wherein the input unit is configured to acquire initial patient position image data of a patient in an initial position from a patient position camera based in a first coordinate system of a patient position camera and to acquire initial X-ray image data of the patient from an X-ray system configured into an initial field of view setting,
wherein the initial patient position image data and the initial X-ray image data are acquired substantially simultaneously;
wherein the processing unit is configured to detect a portion of an item of patient anatomy in the initial X-ray image data, to predict an improved field of view setting for enhanced imaging of the item of patient anatomy in a second coordinate system of the initial X-ray image data, wherein the prediction is provided using an anatomical model, to obtain subsequent patient position image data from the patient position camera, to generate patient position error data by comparing the subsequent patient position image data with the initial patient position image data, and to provide a subsequent field of view setting based on the patient position error data and the improved field of view setting;
wherein the X-ray source, and/or the X-ray detector are configurable into an initial and subsequent view state based upon an initial and a subsequent field of view setting generated by the apparatus.

11. The X-ray imaging system according to claim 10, wherein the patient imaging camera is at least one of a video camera, an infra-red camera, and a depth camera.

12. The X-ray imaging system according to claim 10, further comprising:
a multi-view camera system comprising a plurality of cameras wherein the initial patient position image data is provided using the multi-view camera system.

13. A method for adjusting a field of view of an X-ray imaging system, comprising:
acquiring initial patient position image data of a patient in an initial position from a patient position camera based in a first coordinate system of the patient position camera,
acquiring initial X-ray image data of the patient from an X-ray system configured into an initial field of view setting, wherein the initial patient position image data and the initial X-ray image data are acquired substantially simultaneously;
detecting a portion of an item of patient anatomy in the initial X-ray image data;
predicting an improved field of view setting for enhanced imaging of the item of patient anatomy in a second coordinate system of the initial X-ray image data;
wherein the prediction is provided using an anatomical model;
obtaining subsequent patient position image data from the patient position camera;
generating patient position error data by comparing the subsequent patient position image data with the initial patient position image data; and
providing a subsequent field of view setting based on the patient position error data and the improved field of view setting.

14. A non-transitory computer-readable medium having one or more executable instructions stored thereon which, when executed by at least one processor, cause the at least one processor to perform a method for adjusting a field of view of an X-ray imaging system, comprising:
acquiring initial patient position image data of a patient in an initial position from a patient position camera based in a first coordinate system of the patient position camera;
acquiring initial X-ray image data of the patient from an X-ray system configured into an initial field of view setting, wherein the initial patient position image data and the initial X-ray image data are acquired substantially simultaneously;
detecting a portion of an item of patient anatomy in the initial X-ray image data;
predicting an improved field of view setting for enhanced imaging of the item of patient anatomy in a second coordinate system of the initial X-ray image data, wherein the prediction is provided using an anatomical model;
obtaining subsequent patient position image data from the patient position camera;
generating patient position error data by comparing the subsequent patient position image data with the initial patient position image data; and
providing a subsequent field of view setting based on the patient position error data and the improved field of view setting.

* * * * *